United States Patent [19]

Chari

[11] Patent Number: 5,076,302
[45] Date of Patent: Dec. 31, 1991

[54] APPARATUS FOR AND METHOD OF DISPENSING DENTAL FLOSS

[76] Inventor: Srinivas R. Chari, 214 Lagoon Dr., Northfield, Ill. 60093

[21] Appl. No.: 489,326

[22] Filed: Mar. 5, 1990

[51] Int. Cl.$^5$ ............................................. A61C 15/00
[52] U.S. Cl. ............................................. 132/325; 132/324
[58] Field of Search ............... 132/323, 322, 324, 325, 132/326, 327; 222/80, 93, 192; 215/228; 220/212

[56] References Cited

U.S. PATENT DOCUMENTS

| | | | |
|---|---|---|---|
| 1,050,560 | 1/1913 | Moore | 132/314 |
| 1,733,114 | 10/1929 | Brennan | 132/314 |
| 1,849,769 | 3/1932 | Priest | 132/309 |
| 2,233,522 | 3/1941 | Fickle | 132/325 |
| 3,830,247 | 8/1974 | Kaphalakos | 132/322 |
| 4,019,522 | 4/1977 | Elbreder | 132/322 |
| 4,232,688 | 11/1980 | Day | 132/327 |
| 4,428,389 | 1/1984 | Cordero | 132/325 |
| 4,546,782 | 10/1985 | Kucher | 132/329 |
| 4,673,106 | 6/1987 | Fishman | 222/80 |
| 4,796,783 | 1/1989 | Paulson | 222/80 |
| 4,827,951 | 5/1989 | Grussmark | 132/314 |
| 4,865,481 | 9/1989 | Scales | 401/195 |

*Primary Examiner*—Gene Mancene
*Assistant Examiner*—Michael Lynch
*Attorney, Agent, or Firm*—Wallenstein, Wagner & Hattis, Ltd.

[57] ABSTRACT

A closure (10) for a container, which closure houses a supply of dental floss (20). The closure (10) is adapted for dispensing the dental floss, and may include a tab (40) extending downwardly from the closure (10) for diverting the dental floss (20) towards the interior of the container. In this manner, the diverted dental floss (20) may be wetted by the contents of the container.

10 Claims, 3 Drawing Sheets

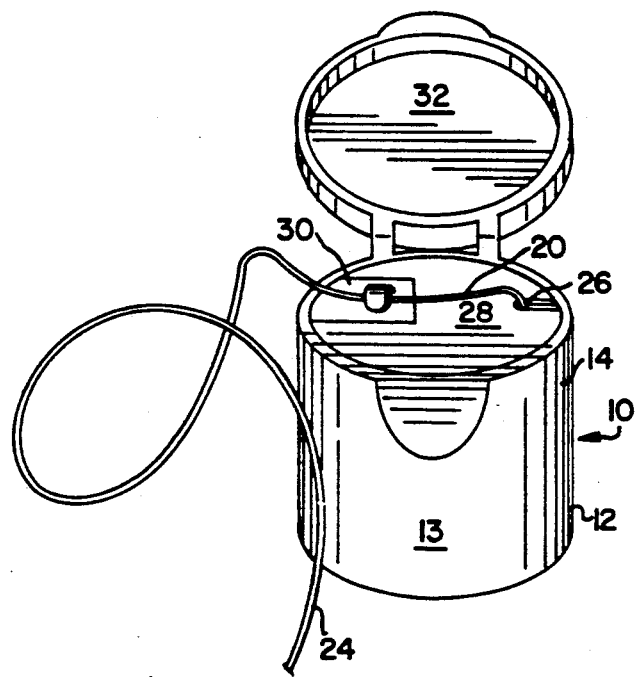
FIG_1_
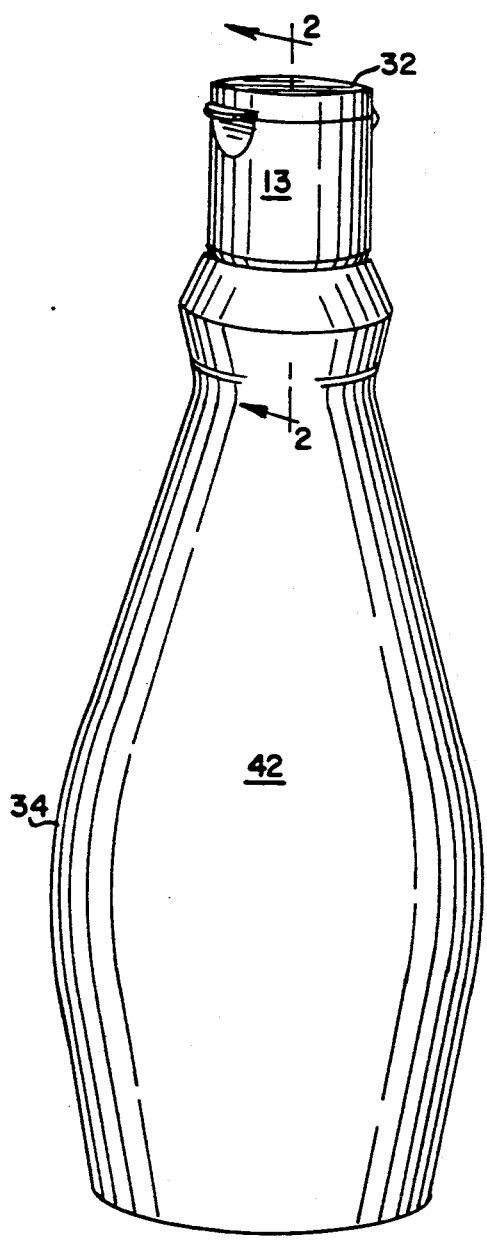
FIG_3_
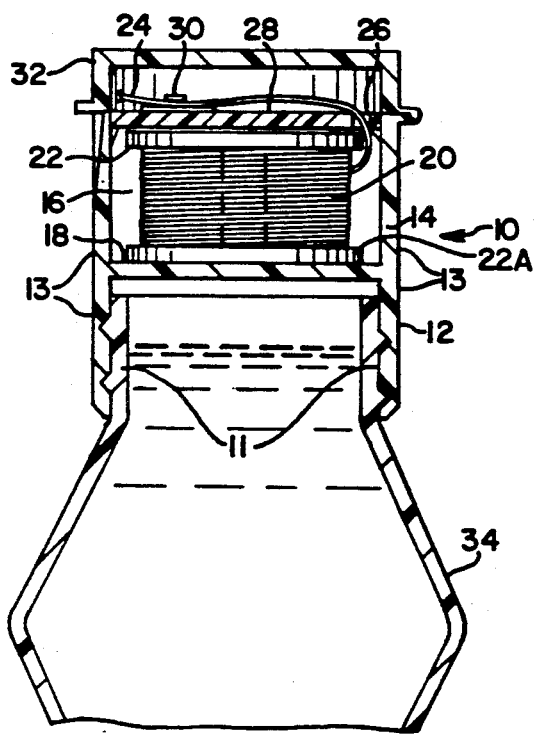
FIG_2_

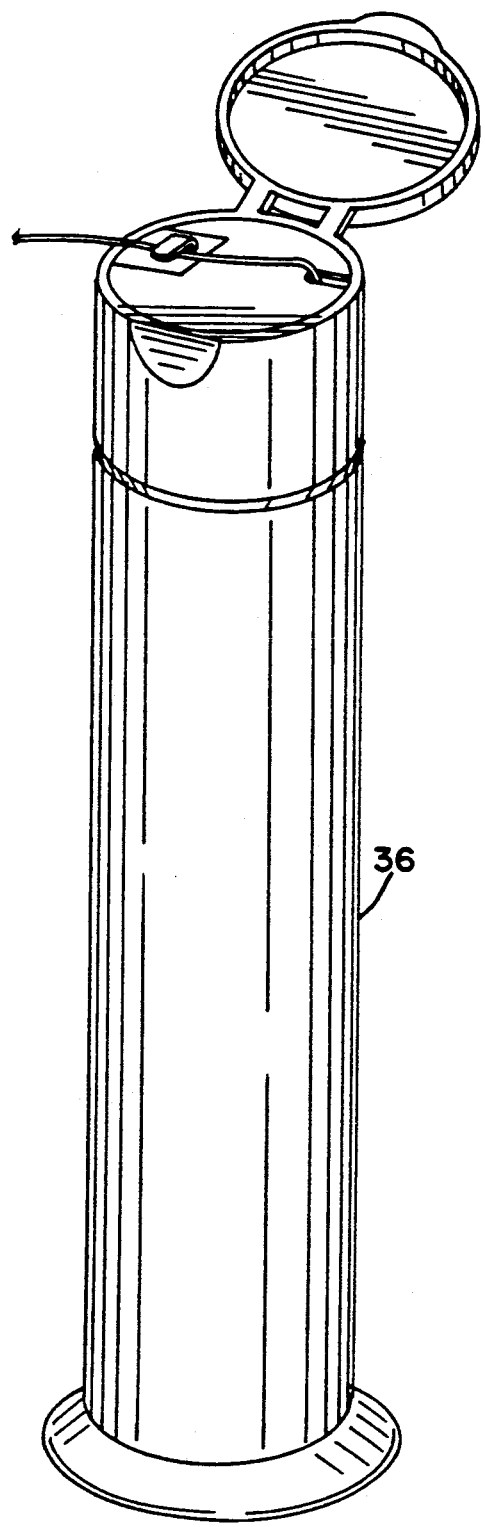
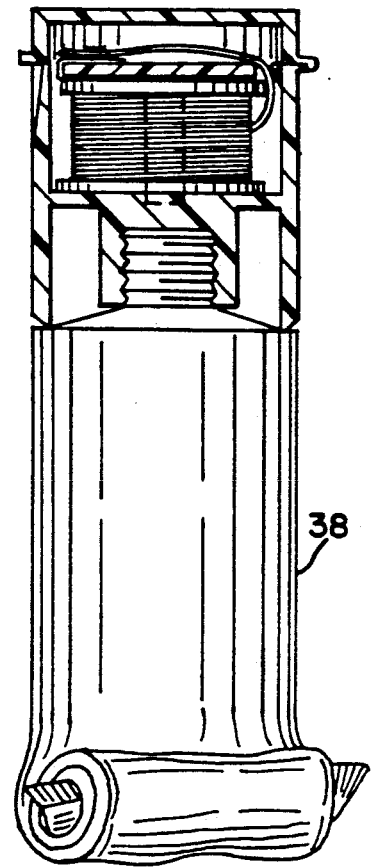
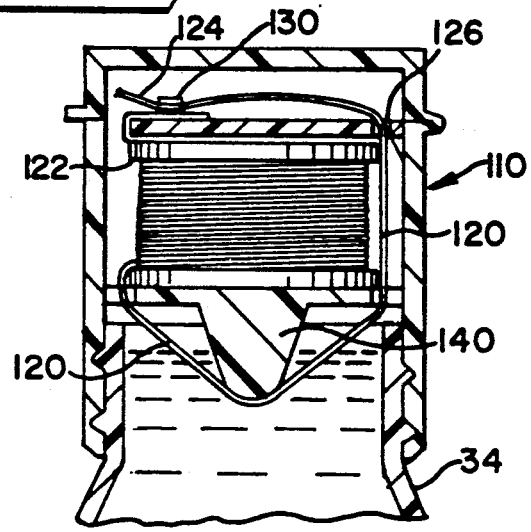

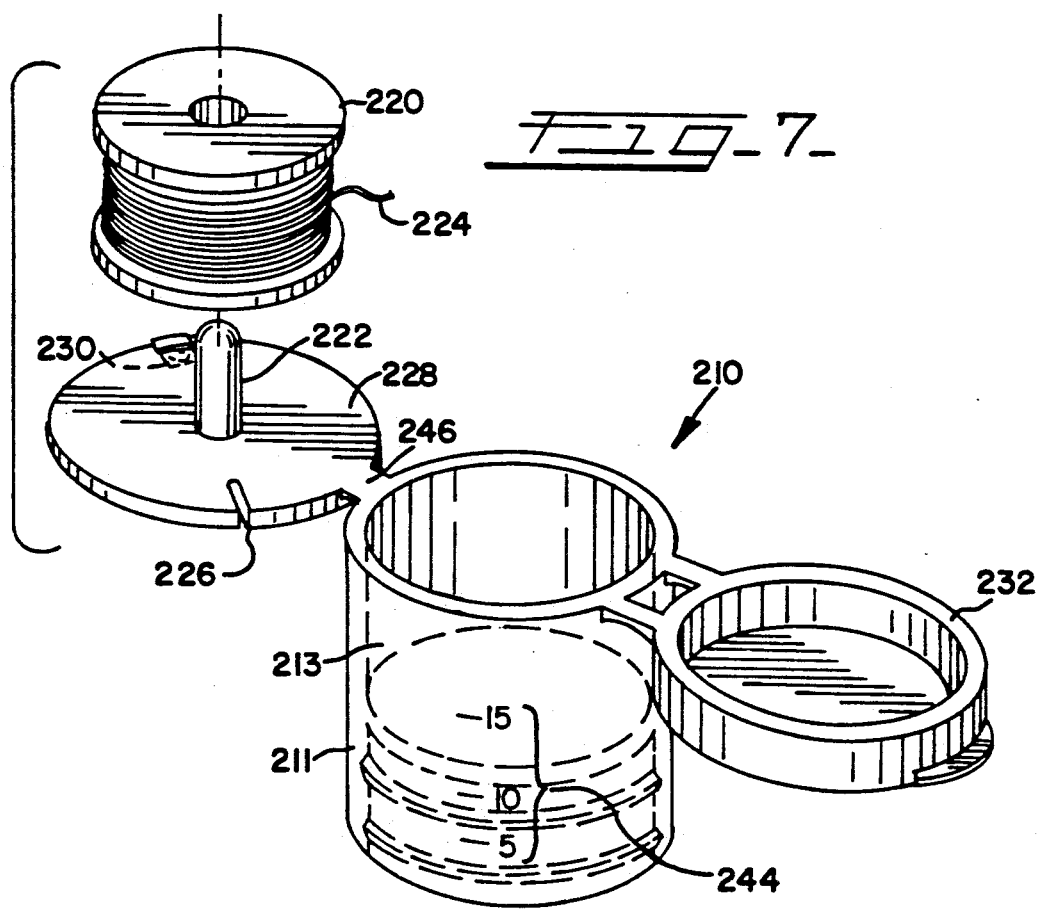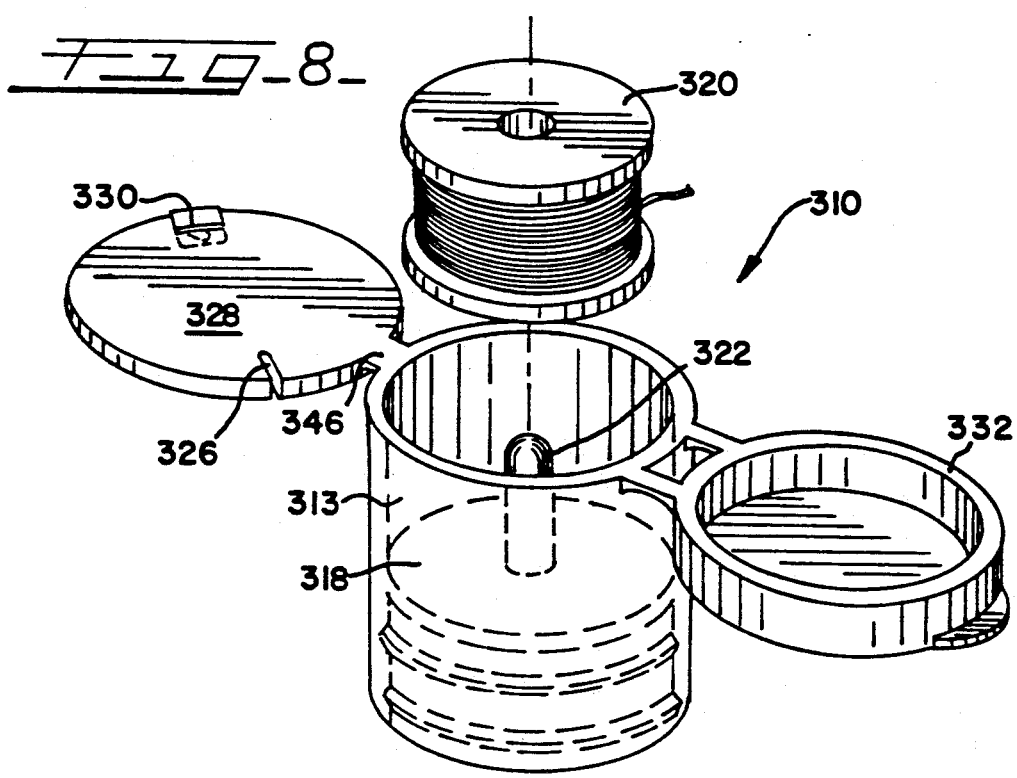

APPARATUS FOR AND METHOD OF DISPENSING DENTAL FLOSS

DESCRIPTION

1. Technical Field

This invention relates generally to product dispensing closures for containers and in particular, to a dental floss dispensing closure for a dentifrice/oral mouthwash container.

BACKGROUND OF THE INVENTION

The advantages of dental flossing are well-known. Flossing dislodges existing plaque, and inhibits further formation of plaque on teeth and gums. Regular flossing also inhibits the onset of periodontal (gum) disease, which can result in premature loss of teeth. Despite these widely known benefits, however, it is estimated that no more than 10% of the American public regularly flosses its teeth. Thus, it is in the health interest of the public to discover new devices and methods that would encourage regular flossing.

Some of the reasons for irregular flossing may be attributable to the containers in which dental floss is currently dispensed. Typically, these containers are small, plastic boxes or cylinders containing from twenty-five to one hundred yards of floss on a spool. The plastic boxes have a hinged lid which may be opened to reveal both the free end of the spooled floss and a floss-cutting anvil. The plastic containers generally include an anvil and a discharge hole along the perimeter or side wall of that container. While generally suitable for their purpose, these small boxes tend to be hidden from view and also tend to be overlooked or misplaced, thereby attributing to the non-use of dental floss by consumers.

Some manufacturers of dentifrice or mouthwash have tried to make dental floss containers more prominent and readily available. For example, manufacturers are known to have dental floss in its normal box-shaped or cylindrical containers attached with banding to a toothpaste tube or mouthwash bottle. However, in order to use the dental floss, its container must typically be removed from the tube or bottle. Thus, any such banding would only remind the user of the need for flossing the first time the toothpaste or mouthwash is used. Thereafter, because the floss container is detached from the tube or bottle, it is as likely to be overlooked or misplaced as any other conventional floss container.

Other manufacturers have attempted to provide solutions to these and other problems. Among them are those disclosed U.S. Pat. Nos. 1,050,560; 1,849,769; 1,733,114; 3,830,247; 4,019,522; 4,428,389; 4,673,106; 4,796,783; 4,827,951 and 4,865,481.

However, prior to the present invention, a need existed for a floss dispensing closure to a dentifrice or oral wash container in which the cover to the closure is integrally hinged to the closure. A need existed for a floss dispensing closure which diverts a segment of floss through the neck of an oral wash container to rinse the floss segment with oral wash.

SUMMARY OF THE INVENTION

The invention is a closure for a container which includes a compartment for housing a supply of dental floss. Means are provided for dispensing the dental floss from that closure. In one preferred embodiment, the closure is provided with means for diverting the floss towards the interior of the container. For example, these means may include a tab extending downwardly from the closure. The diverted dental floss may be wetted by the contents of the container, whether those contents are mouthwash, toothpaste, or some other substance conducive to good oral hygiene.

Another preferred embodiment may include a cutting anvil for the dental floss near the top of the closure. Moreover, the closure may be provided with a cover integrally hinged to the closure for the protection of the dental floss and the anvil when the dental floss is not being dispensed.

The invention is also a method of dispensing an oral mouthwash or a dentifrice or the like from a container. The method includes extending a segment of dental floss into the container. The dental floss is next urged into contact with the oral mouthwash or dentifrice, resulting in the formation of a segment of mouthwash- or dentifrice-coated dental floss. One such method of urging the oral mouthwash into contact with the floss is by inverting the bottle. This results in wetting of the floss by the rinse. Finally, the mouthwash- or dentifrice-coated dental floss is removed from the oral mouthwash or the dentifrice and the container. Upon removal of the dental floss, the mouthwash- or dentifrice-covered floss may be used in the conventional manner by a user.

Other advantages and aspects of the invention will become apparent upon making reference to the specification, claims, and drawings to follow.

BRIEF DESCRIPTION OF THE DRAWINGS

FIG. 1 is a perspective view of a closure in accordance with one embodiment of the invention;

FIG. 2 is a side sectional view of the closure of FIG. 1, taken along lines 2—2 of FIG. 3;

FIG. 3 is a perspective view of the closure of FIG. 1, and on a container for an oral mouthwash;

FIG. 4 is a perspective view of a closure in accordance with the invention, but on a toothpaste pump;

FIG. 5 is a perspective view of a closure in accordance with the invention on a collapsible toothpaste tube, with a threaded inner portion for securing that closure to a complementary threaded portion of that toothpaste tube;

FIG. 6 is a cross-sectional view of another preferred embodiment of the invention, and including tab means for diverting dental floss contained within its well towards the interior of a mouthwash container;

FIG. 7 is a perspective view of another embodiment of the invention, and shown in an opened position; and, FIG. 8 is a perspective view of a still further embodiment of the invention.

DETAILED DESCRIPTION OF THE INVENTION

While this invention is susceptible of embodiment in many different forms, there is shown in the drawings and will herein be described in detail a preferred embodiment of the invention with the understanding that the present disclosure is to be considered as an exemplification of the principles of the invention and is not intended to limit the broad aspect of the invention to embodiment illustrated.

One embodiment of the invention, shown in perspective view in FIG. 1, is a novel closure 10 for a container. Closure 10 is best suited for containers for products that enhance oral hygiene, such as a toothpaste tube or pump, or a mouthwash bottle. Closure 10 may be made of any of the suitable and conventional materials of which conventional closures are now made, such as an appropriate plastic, and may be either opaque, as shown in FIGS. 1-3, or transparent.

Closure 10 of FIG. 1 is shown alone, and without the container upon which it is intended to be used. In addition to acting as a sealing means for a container, closure 10 also serves to provide a housing for the storage and retrieval of dental floss. In this embodiment, the closure 10 may be an integrally molded, one-piece or two-piece unit.

Closure 10 comprises two distinct portions. The first is a threaded lower portion 12, generally similar to a conventional screw-on cap. In this embodiment, threaded lower portion 12 serves as the sealing means for the sealing of the container upon which the closure is normally housed. Threads 11 are formed along the inner portion of the peripheral wall 13 of closure 10.

The second portion is an overcap 14 having a contained, generally hollow well portion 16 (FIG. 2). The generally flat top 18 of the threaded lower portion 12 forms the floor of the well portion 16 and overcap 14. It will be understood by those skilled in the art, however, that the cap 12 and the overcap 14 of the present invention could comprise two components: a conventional screw-on cap, which would comprise the sealing means for the sealing of the container upon which the closure is normally housed, and a separate and distinct overcap that is compression-fit onto this screw-on cap. It will also be understood by those skilled in the art that the closure 10 need not be threaded onto its container, but rather may be snapped onto that container, or secured to that container in any other suitable manner.

The well portion 16 is suited for housing the supply of dental floss 20. The closure 10 also includes means for dispensing the dental floss from its well portion 16. These dispensing means, in accordance with the present invention, may include any suitable arrangement which enables the floss 20 to be removed from the well portion 16 of the closure.

In this embodiment, as may be seen in FIG. 2, these dispensing means for the floss 20 include a cylindrical spool 22 around which the floss 20 is wound, in a manner generally similar to the winding of floss in conventional containers. The spool 22 disclosed in FIG. 2 has end caps 22A although it is also known in the art to simply wind floss around a bobbin core which has no end caps.

A free end 24 of floss 20 is dispensed through a peripheral edge groove 26 formed in the top 28 of the overcap 14. The top 28 of the overcap 14 may itself be removably secured to that overcap. Alternatively, it may be fixedly secured, as by molding the top 28 as an integral portion of the overcap 14. If the top 28 is removably secured to the overcap 14, then that top 28 may be removed to disclose the well 16 and the floss 20 contained within the well 16. For this reason, a removably secured top 28 is preferable in closures that are molded as one piece.

The closure may also include a cutting anvil 30 for the dental floss 20. As may be seen in FIG. 1, this cutting anvil 30 is conventional, and serves to both cut the floss 20 as it is dispensed through groove 26 and retain the floss 20 in a secured position along the top 28 of overcap 14 when not being dispensed. The closure 10 may further include a hinged cover 32 for the protection of the dental floss 20 and the cutting anvil 30 when the dental floss is not being dispensed.

In a second embodiment of the invention, shown in FIG. 6, a slightly different closure 110 comprises, in addition to the components of closure 10, means for diverting the dental floss 120 towards the interior of the container on which the closure 110 is positioned. Both this closure 110 of the second embodiment and closure 10 of the first embodiment are suitable for many containers for products which enhance oral hygiene, including the containers shown in FIGS. 3, 4, and 5. The containers shown in these three FIGS. are, respectively, a mouthwash bottle 34, a toothpaste pump 36, and a toothpaste tube 38.

Many dentifrices and some brands of mouthwash have been shown effective in reducing plaque. Thus, the use of dental floss that is coated with a plaque-reducing or anti-microbial substance may have a superior plaque-inhibiting and therapeutic effect than the use of the floss alone. For this reason, the diverting means of the closure 110 of this second embodiment are intended to divert the dental floss 120 towards the interiors of any of these containers 34, 36, and 38. In this manner, the floss 120 will contact the dentifrice or mouthwash prior to its dispensation from the closure 110. From the above, it is apparent that the present closure 110, when used in this manner, also serves to dispense a dentifrice or a mouthwash.

As shown in FIG. 6, a particular means for diverting the dental floss 120 may comprise a tab 140 extending downwardly from the closure 110. The closure 110 is shown in FIG. 3 on a mouthwash bottle 34 made of a resilient, compressible plastic. When the user compresses the compressible sides 42 of bottle 34 to effectively decrease its volume, the level of the mouthwash in the bottle 34 rises to the level of the tab 140, as shown in FIG. 6. In this manner, the diverted dental floss 120 adjacent that tab 140 is wetted and coated by the contents of the mouthwash bottle 34. It will be apparent that rather than compressing the sides 42 of the bottle, the floss 20 may also be coated with mouthwash by shaking or momentarily inverting that bottle 34.

When a user pulls upon the free end 124 of the floss 120, a desired length of coated floss 120 is discharged from the closure 110. As that user retrieves this length of coated floss, new floss is uncoiled from its cylindrical spool 122, moves downwardly towards the tab 140, and then back upwardly and towards groove 126 and cutting anvil 130. In this manner, another length of floss is readied and positioned for coating by a subsequent user.

When the tab 140 of this second embodiment is used with a toothpaste pump 36 or tube 38, there will ordinarily be no need to compress, shake, or invert those containers. The tab 140 used for such containers would normally be positioned at their upper ends, similarly to the tab 140 of the closure 110 shown secured to mouthwash bottle 34. Because toothpaste is likewise dispensed from the upper end of the pump 36 or tube 38, the floss would necessarily be covered with toothpaste as it was removed from the closure 110.

The embodiments of FIGS. 7 and 8 disclose a preferred method of assembling the closure of the present invention. FIG. 7 discloses a closure 210 formed from a cylindrical peripheral wall 213 having threads 211 formed along a lower portion thereof. Volumetric graduations 244 are stamped or printed along the inside wall of the closure. These graduations include numerals corresponding to either ounces, milliliters, or fractional dosages. In this way, an oral rinse or mouthwash may be poured into the inverted closure 210, and graduations 244 may be used to determine the proper or desired amount of mouthwash.

Closure 210 also includes an overcap top 228 which is secured to the peripheral wall 213 by a living hinge 246. A spindle 222 is secured or molded into top 228, as shown in FIG. 7. In assembling the embodiment of FIG. 7, floss spool 220 is first placed onto spindle 222. Free end 224 of the floss on spool 220 may then be inserted through a peripheral edge groove 226. Free end 224 is drawn from groove 226 over top 228 and placed in severably contact with edge 230. Opposed from groove 226 is a cutting edge 230. The top 228 is then pivoted about the hinge 246 until it snaps into place on the closure 210 at the top of the peripheral wall 213.

A hinged cover 232 is also provided. The hinged cover 232 finds particular utility in embodiments (not shown) where a groove and a cutting edge are carried on the top 228, and the dental floss extends between this groove and cutting anvil. In such embodiments, hinged cover 232 protects the floss when not in use.

FIG. 8 discloses an embodiment slightly different form the FIG. 7 embodiment. In this embodiment, a spindle 322 is secured or molded to a floor 318 of a closure 310. Like the embodiment of FIG. 7, a floss spool 320 is placed over a spindle 322. A free end 324 of a floss spool 320 may then be inserted through groove 326 and placed in severable contact with opposed cutting edge 330. An overcap top 328 is then pivoted about a living hinge 346 until it snaps into place on the closure 310 at the top of the peripheral wall 313. A cover 332, hingeably joined to closure 310 is then pivoted to enclose top 328.

A method of dispensing and coating dental floss with oral mouthwash or a dentifrice in accordance with the present invention comprises the following steps with reference generally to FIG. 6. First, a segment of dental floss 20 is extended into the container, such as containers 34, 36, or 38. Second, the dental floss 20 is urged into an upper portion or neck of the container. This can be achieved by compressing or inverting the container. As a result, floss 20 contacts the oral mouthwash or dentifrice to thereby coat a segment of dental floss with the mouthwash or dentifrice. Finally, the coated dental floss is removed from the dispensing closure and the coated floss is then in condition for use by a user.

While the specific embodiments have been illustrated and described, numerous modifications come to mind without markedly departing from the spirit of the invention. The scope of protection is thus only intended to be limited by the scope of the accompanying claims.

What I claim is:

1. A dental floss dispensing closure for a container of dentifrice or oral mouthwash, the closure comprising:
   a. a housing containing a supply of dental floss;
   b. means for dispensing said dental floss from said housing;
   c. cutting means for cutting said dental floss;
   d. a cover joined to the closure for the protection of said dental floss and said cutting means when said dental floss is not being dispensed;
   e. a peripheral wall, and threads formed along the inner portion of said peripheral wall; and
   f. means for diverting said dental floss towards the interior of said container.

2. The closure as set forth in claim 1, wherein said diverting means comprise a tab extending downwardly from said closure along which said dental floss passes.

3. A dental floss dispensing closure for a container of oral rinse, said closure housing a supply of dental floss, said closure comprising:
   a. a peripheral wall;
   b. means for fastening the closure to the container, said means for fastening being formed along the inner portion of one end of said peripheral wall;
   c. means for dispensing said dental floss from another end of said peripheral wall;
   d. means for diverting said dental floss inwardly into said container, said means for diverting extending from the one end of the peripheral wall;
   e. cutting means to both cut the dental floss when being dispensed and to retain the dental floss in a secured position when not being dispensed; and
   f. a cover hingeably joined to the other end of the peripheral wall, the cover being for the protection of said dental floss and said cutting means when said dental floss is not being dispensed.

4. A one piece dental floss dispensing closure for the top of a container, said closure comprising:
   a peripheral wall, said peripheral wall including threads formed along an inner portion of one end of said peripheral wall;
   an overcap top hingeably joined to an other end of said peripheral wall, the overcap top having a topside surface and a bototmside surface;
   a cover hingeably joined to said peripheral wall and spatially disposed from the overcap top, the cover being pivotable to overlay the overcap top; and,
   a spool rotatably carried on the bottomside surface of said top.

5. The closure set forth in claim 4 wherein the spool is carried on a spindle centrally extending from the bottomside of the overcap top, said spindle extending within said closure at a level entirely above the top of said container.

6. A dental floss dispensing closure for a container, said closure comprising:
   a. a peripheral wall, said peripheral wall including threads formed along an inner portion of one end of said peripheral wall;
   b. an overcap top joined to an other end of said peripheral wall, the overcap top having a topside surface and a bottomside surface;
   c. a cover joined to said peripheral wall being spatially disposed from the overcap top, the cover being pivotable to overlay the overcap top;
   d. a spool rotatably carried on the bottomside surface of said top; and
   e. molded-in markings along an inside portion of said closure for enabling measurement of a specified amount of a liquid.

7. A one piece dental floss dispensing closure for a container, said closure comprising:
   a peripheral wall including threads formed along an inner portion of one end of said peripheral wall;
   an overcap top hingeably joined to an other end of said peripheral wall;
   a cover hingeably joined to said peripheral wall and axially opposed from the overtop cap, the cover being pivotable to overlay the overcap top;
   a spool rotatably carried on a floor of said closure.

8. A dental floss dispensing closure for a container, said closure comprising:

a. a peripheral wall, said peripheral wall including threads formed along an inner portion of one end of said peripheral wall;

b. an overcap top hingeably joined to another end of said peripheral wall;

c. a cover hingeably joined to said peripheral wall and spatially disposed from the overtop cap, the cover being pivotable to overly the overcap top;

d. a spool rotatably carried on a floor of said closure; and e. molded-in markings along an inside portion of said closure for enabling measurement of a specified amount of a liquid.

9. A dental floss dispensing closure for a container, said closure comprising:

a. a peripheral wall, said peripheral wall including threads formed along an inner portion of one end of said peripheral wall;

b. an overcap top joined to an other end of said peripheral wall, the overcap top having a topside surface and a bottomside surface;

c. a cover joined to said peripheral wall being spatially disposed from the overcap top, the cover being pivotable to overlay the overcap top;

d. a spool rotatably carried on the bottomside surface of said top; and e. means for measuring and dispensing dental hygiene medicaments.

10. A dental floss dispensing closure for a container, said closure comprising:

a. a peripheral wall, said peripheral wall including threads formed along an inner portion of one end of said peripheral wall;

b. an overcap top hingeably joined to another end of said peripheral wall;

c. a cover hingeably joined to said peripheral wall and spatially disposed from the overtop cap, the cover being pivotable to overly the overcap top;

d. a spool rotatably carried on a floor of said closure; and e. means for measuring and dispensing dental hygiene medicaments.

* * * * *

UNITED STATES PATENT AND TRADEMARK OFFICE
CERTIFICATE OF CORRECTION

PATENT NO. : 5,076,302
DATED : December 31, 1991
INVENTOR(S) : Srinivas R. Chari It is certified that error appears in the above-identified patent and that said Letters Patent is hereby corrected as shown below:

Column 5, line 13, delete "severably" and insert --severable--.

Column 5, line 24, delete "form" and insert --from--.

Column 6, Claim 4, line 30, delete "bototmside" and insert --bottomside--.

Column 7, Claim 8, line 8, delete "overly" and insert --overlay--.

Column 8, Claim 10, line 16, delete "overtop cap" and insert --overcap top--.

Column 8, Claim 10, line 17, delete "overly" and insert --overlay--.

Signed and Sealed this

Twentieth Day of April, 1993

Attest:

MICHAEL K. KIRK

*Attesting Officer*    Acting Commissioner of Patents and Trademarks